United States Patent
Wu et al.

(10) Patent No.: US 7,229,591 B2
(45) Date of Patent: *Jun. 12, 2007

(54) LUMEN STERILIZATION DEVICE AND METHOD

(75) Inventors: Su-Syin S. Wu, Irvine, CA (US); Harold R. Williams, San Clemente, CA (US); Nancy S. Chu, Laguna Niguel, CA (US); Hans Strobel, Zurich (CH); Szu-Min Lin, Laguna Hills, CA (US); Henry K. Hui, Laguna Niguel, CA (US); Leslie A. Feldman, Calabasas Hills, CA (US)

(73) Assignee: Ethicon, Inc., Somerville, NJ (US)

( * ) Notice: Subject to any disclaimer, the term of this patent is extended or adjusted under 35 U.S.C. 154(b) by 593 days.

This patent is subject to a terminal disclaimer.

(21) Appl. No.: 10/160,869

(22) Filed: May 31, 2002

(65) Prior Publication Data

US 2003/0026729 A1     Feb. 6, 2003

Related U.S. Application Data

(63) Continuation-in-part of application No. 09/746,990, filed on Dec. 22, 2000, which is a continuation-in-part of application No. 09/384,761, filed on Aug. 27, 1999, now Pat. No. 6,187,265, which is a continuation of application No. 08/992,131, filed on Dec. 17, 1997, now abandoned, application No. 10/160,869, which is a continuation-in-part of application No. 09/472,319, filed on Dec. 23, 1999, now Pat. No. 6,451,255, which is a continuation-in-part of application No. 08/915,922, filed on Aug. 21, 1997, now Pat. No. 6,066,294.

(51) Int. Cl.
*A61L 2/00* (2006.01)

(52) U.S. Cl. .......................... 422/33; 422/28; 422/292; 134/170

(58) Field of Classification Search .................. 422/28, 422/33, 292, 300, 297, 305; 134/84, 170
See application file for complete search history.

(56) References Cited

U.S. PATENT DOCUMENTS

| 3,393,680 | A | 7/1968 | Curutchet |
| 3,814,901 | A | 6/1974 | Morhack |
| 3,913,588 | A | 10/1975 | Baumgarten |
| 4,203,943 | A | 5/1980 | Gillis et al. |
| 4,321,232 | A | 3/1982 | Bithell |
| 4,337,223 | A | 6/1982 | Kaye ........................ 422/112 |
| 4,380,530 | A | 4/1983 | Kaye |
| 4,410,492 | A | 10/1983 | Kaye .......................... 422/33 |
| 4,525,220 | A | 6/1985 | Sasa et al. ................... 134/21 |
| 4,526,622 | A | 7/1985 | Takamura et al. ............ 134/21 |

(Continued)

FOREIGN PATENT DOCUMENTS

DE        3416743        7/1985

(Continued)

*Primary Examiner*—Gladys JP Corcoran
*Assistant Examiner*—Sean E. Conley

(57) ABSTRACT

Devices and methods for sterilizing lumens involve a booster that is attached to the lumen. In preferred embodiments, the contact area between the lumen and the booster enhances the penetration of an antimicrobial agent to the contact area.

7 Claims, 7 Drawing Sheets

U.S. PATENT DOCUMENTS

| | | | |
|---|---|---|---|
| 4,576,792 A | 3/1986 | Martensson | |
| 4,579,597 A | 4/1986 | Sasa et al. | 134/21 |
| 4,579,598 A | 4/1986 | Sasa et al. | 134/22.12 |
| 4,643,876 A | 2/1987 | Jacobs et al. | 422/23 |
| 4,731,222 A | 3/1988 | Kralovic et al. | |
| 4,744,951 A | 5/1988 | Cummings et al. | |
| 4,756,882 A | 7/1988 | Jacobs et al. | 422/23 |
| 4,797,255 A | 1/1989 | Hatanaka | |
| 4,863,688 A | 9/1989 | Schmidt | |
| 4,892,706 A | 1/1990 | Kralovic et al. | |
| 4,937,046 A | 6/1990 | Andersen et al. | |
| 4,943,414 A | 7/1990 | Jacobs et al. | 422/28 |
| 4,956,145 A | 9/1990 | Cummings et al. | 422/28 |
| 5,017,241 A | 5/1991 | Ryan | |
| 5,037,623 A | 8/1991 | Schneider et al. | |
| 5,077,008 A | 12/1991 | Kralovic et al. | |
| 5,084,239 A | 1/1992 | Moulton et al. | 422/22 |
| 5,091,343 A | 2/1992 | Schneider et al. | |
| 5,114,596 A | 5/1992 | Laterra | |
| 5,116,575 A | 5/1992 | Badertscher et al. | |
| 5,118,471 A | 6/1992 | Andersen | |
| 5,122,344 A | 6/1992 | Schmoegner | |
| 5,176,699 A | 1/1993 | Markham | |
| 5,188,893 A | 2/1993 | Moulton et al. | 422/23 |
| 5,209,909 A | 5/1993 | Siegel et al. | |
| 5,217,698 A | 6/1993 | Siegel et al. | |
| 5,225,160 A | 7/1993 | Sanford et al. | |
| 5,227,132 A | 7/1993 | Andersen | |
| 5,244,629 A | 9/1993 | Caputo et al. | 422/22 |
| 5,260,021 A | 11/1993 | Zelenznick | |
| 5,266,275 A | 11/1993 | Faddis | |
| 5,269,790 A | 12/1993 | Funatsu | 606/142 |
| 5,288,460 A | 2/1994 | Caputo et al. | 422/23 |
| 5,297,799 A | 3/1994 | Slater et al. | |
| 5,310,524 A | 5/1994 | Campbell et al. | 422/27 |
| 5,348,711 A | 9/1994 | Johnson et al. | |
| 5,350,563 A | 9/1994 | Kralovic et al. | |
| 5,374,394 A | 12/1994 | Kralovic et al. | |
| 5,391,360 A | 2/1995 | Kochte et al. | |
| 5,407,685 A | 4/1995 | Malchesky et al. | |
| 5,413,758 A | 5/1995 | Caputo et al. | 422/22 |
| 5,441,707 A | 8/1995 | Lewis et al. | |
| 5,443,801 A | 8/1995 | Langford | |
| 5,445,792 A | 8/1995 | Rickloff et al. | |
| 5,447,684 A | 9/1995 | Williams | |
| 5,492,671 A | 2/1996 | Kraft | 422/26 |
| 5,494,530 A | 2/1996 | Graf | |
| 5,505,218 A | 4/1996 | Steinhauser et al. | |
| 5,508,009 A | 4/1996 | Rickloff et al. | |
| 5,527,508 A | 6/1996 | Childers et al. | |
| 5,534,221 A | 7/1996 | Hillebrenner et al. | |
| 5,534,222 A | 7/1996 | Kelbrick | |
| 5,540,901 A | 7/1996 | Riley | |
| 5,552,115 A * | 9/1996 | Malchesky | 422/28 |
| 5,556,607 A | 9/1996 | Childers et al. | |
| 5,580,530 A | 12/1996 | Kowatsch et al. | 422/292 X |
| 5,609,821 A | 3/1997 | Grimberg et al. | |
| 5,620,427 A | 4/1997 | Werschmidt et al. | |
| 5,633,424 A | 5/1997 | Graves | |
| 5,641,464 A | 6/1997 | Briggs, III | |
| 5,667,753 A | 9/1997 | Jacobs | |
| 5,711,921 A | 1/1998 | Langford | |
| 5,733,503 A | 3/1998 | Kowatsch et al. | 422/28 |
| 5,776,146 A | 7/1998 | Jones | |
| 5,846,484 A | 12/1998 | Scarborough | |
| 6,083,458 A | 7/2000 | Lin et al. | 422/33 |
| 6,090,213 A | 7/2000 | Moyers | |
| 6,120,729 A | 9/2000 | Schad | |
| 6,162,395 A | 12/2000 | Kowanko | 422/33 |
| 6,187,265 B1 * | 2/2001 | Wu et al. | 422/28 |
| 6,312,646 B2 | 11/2001 | Kowanko | 422/33 |
| 6,365,103 B1 | 4/2002 | Fournier | 422/33 |
| 6,451,255 B1 * | 9/2002 | Williams et al. | 422/33 |

FOREIGN PATENT DOCUMENTS

| | | |
|---|---|---|
| JP | 58-1801-30 | 10/1983 |
| WO | WO 96/30058 | 10/1996 |

* cited by examiner

OPENED POSITION AT 90° DEGREE

CLOSED POSITION

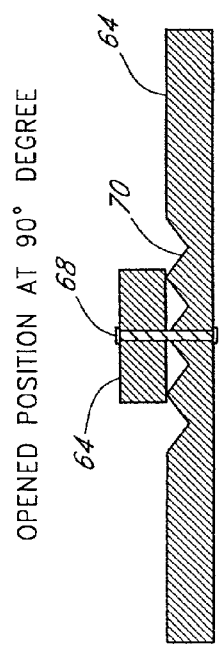
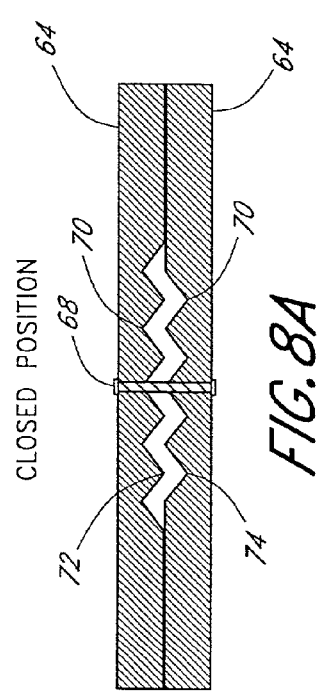
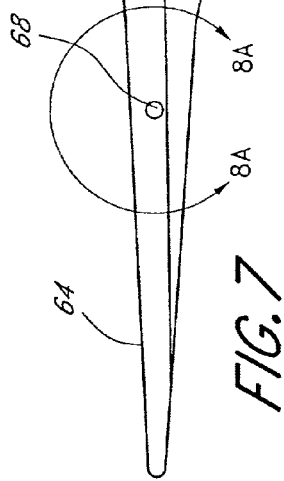
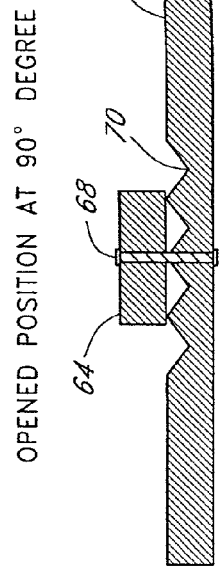
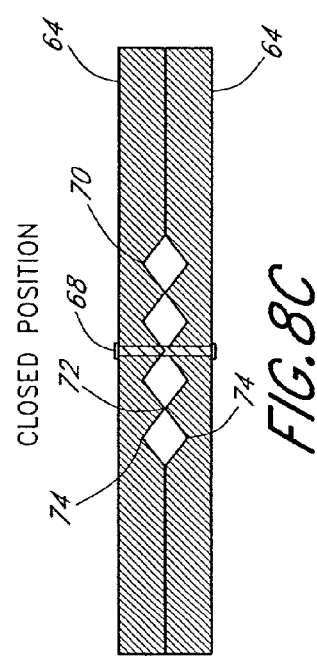
FIG.8B OPENED POSITION AT 90° DEGREE
FIG.8D OPENED POSITION AT 90° DEGREE
FIG.7
FIG.8A CLOSED POSITION
FIG.8C CLOSED POSITION

LUMEN STERILIZATION DEVICE AND METHOD

RELATED APPLICATION INFORMATION

This application is a continuation-in-part of U.S. application Ser. No. 09/746,990, filed Dec. 22, 2000, which is a continuation-in-part of U.S. application Ser. No. 09/384,761, filed Aug. 27, 1999, now U.S. Pat. No. 6,187,265; which is a continuation of U.S. application Ser. No. 08/992,131, filed Dec. 17, 1997, now abandoned, all of which are hereby incorporated by reference in their entireties. This application is also a continuation-in-part of U.S. application Ser. No. 09/472,319, filed Dec. 23, 1999, now U.S. Pat. No. 6,451,255, which is a continuation-in-part of U.S. application Ser. No. 08/915,922, filed Aug. 21, 1997, now U.S. Pat. No. 6,066,294, all of which are hereby incorporated by reference in their entireties.

BACKGROUND OF THE INVENTION

1. Field of the Invention

This invention relates to the sterilization of medical devices. In particular, this invention relates to systems, methods and devices for sterilizing lumens.

2. Description of the Related Art

Articles such as medical instruments are normally sterilized before use. There are many methods of sterilizing medical equipment, including heat treatment and chemical methods. Heat sterilization is normally performed with steam. Some equipment cannot withstand either the heat or the moisture from steam treatment. As a result, chemical sterilization is now commonly used.

Chemical sterilization uses a sterilizing fluid such as hydrogen peroxide, ethylene oxide, chlorine dioxide, peracetic acid, formaldehyde, or a combination thereof. A plasma may be induced to enhance the sterilization process. Although chemical sterilization is normally highly effective, it may not be as effective with medical devices having long, narrow tubes, or lumens. It is difficult for the sterilizing agent to completely penetrate and sterilize these long narrow tubes. In order to enhance the penetration of the sterilizing agent down the entire length of the lumen, several methods and several forms of apparatus have been developed to flow sterilizing agent through the length of the lumen, enhancing the effectiveness of the sterilizing treatment.

For example, U.S. Pat. Nos. 4,410,492 and 4,337,223 describe an apparatus and a method for sterilizing lumens in which the lumen is placed in a socket connected to a circulating pump. The pump circulates the sterilizing gas through the lumen. Although the method is effective in sterilizing the lumen, the commercial apparatus uses ethylene oxide as a sterilant, and sterilization requires times of about 2–3 hours. Ethylene oxide is toxic. Additional aeration time is needed to remove the residual.

U.S. Pat. No. 5,580,530 describes a method for delivering sterilizing agent through long, narrow lumens. The lumen is inserted into an adaptor connected to a vessel containing hydrogen peroxide. The vessel is called a booster. The lumen, adaptor, and booster are placed in a sterilization chamber. When the sterilization chamber is evacuated during the sterilization procedure, the hydrogen peroxide in the booster vaporizes and passes through the lumen, sterilizing the interior of the lumen.

An apparatus and a method for delivering sterilizing agent directly into long, narrow lumens is described in U.S. Pat. Nos. 4,943,414, 5,580,530 and 5,733,503. The lumen is inserted into an adaptor connected to a small vessel containing hydrogen peroxide. The adaptor and the vessel which contains the hydrogen peroxide are called the booster. The lumen, vessel, and adaptor are placed into a sterilization chamber. When the sterilization chamber is evacuated, the hydrogen peroxide vaporizes and passes through the lumen, providing the necessary hydrogen peroxide to the interior of the lumen. Although effective, the method has some disadvantages. First, in some forms of the apparatus, the booster must be "activated" manually by piercing a septum to make the hydrogen peroxide liquid accessible. Second, the booster is used only once before it is discarded. Third, the product has a limited shelf life. The storage and shipping conditions may affect the shelf life of the product.

In each of these sterilization methods, the lumen is held by a connecting device, a socket in the case of U.S. Pat. Nos. 4,410,492 and 4,337,223 or a truncated cone adaptor when using the method of U.S. Pat. No. 5,580,530. In all of these methods, there are areas of contact between the device and the lumen in the area where the lumen attaches to the connecting device. It is difficult for the sterilizing agent to penetrate into these contact areas. There is a need for an apparatus and a method of enhancing the penetration of sterilizing gas or vapor into these contact areas more effectively to allay any potential concerns about incomplete sterilization.

There are also contact areas between the parts of medical devices having two or more pieces. It is difficult to sterilize the contact areas between the parts which make up the medical device. There is a need for a method and an apparatus for enhancing the penetration of sterilant into the contact areas between the pieces which make up the medical device.

There is also a need for a method of sterilizing lumens which does not require the use of a booster with limited shelf life. Further, there is a need for a method which utilizes an apparatus which is reusable, to reduce costs.

SUMMARY OF THE INVENTION

In accordance with one aspect of the invention, an apparatus for sterilizing a lumen comprises a booster and a connecting device between the booster and the lumen, wherein the connecting device comprises a silicone material. Preferably, the connecting device comprises textured or uneven surfaces. In alternative preferred embodiments, the booster comprises a vessel containing an antimicrobial fluid, or the booster is a dry booster.

In accordance with another aspect of the invention, an apparatus for sterilizing a lumen comprises a dry booster and a connecting device between the dry booster and the lumen, wherein the lumen contacts the connecting device at a contact area and wherein the contact area is adapted to enhance penetration of an antimicrobial vapor or gas to the contact area. Preferably, the connecting device is constructed from a material, at least in the contact area, that is permeable to the antimicrobial vapor or gas, and/or the surface of the connecting device in the contact area is textured or uneven. Preferably, the dry booster encloses an internal volume that is greater than the internal volume of the lumen. Preferably, the dry booster comprises a flow restrictor and/or a check valve.

In accordance with another aspect of the invention, a system for sterilizing a lumen comprises: a vacuum chamber; a pump to evacuate the chamber; a dry booster attachable to and detachable from a lumen; and a source of germicide. Preferably, the dry booster comprises an adaptor that contacts the lumen in a contact area; more preferably, the adaptor is constructed from a material, at least in the contact area, that is permeable to a germicide. Preferably, the adaptor comprises a surface that is textured or uneven in the contact area. Preferably, the dry booster encloses an internal volume that is greater than the internal volume of the lumen. Preferably, the dry booster comprises a flow restrictor and/or a check valve.

In accordance with another aspect of the invention, a method for sterilizing a lumen comprises providing a dry booster, a connecting device, and a lumen; connecting a first end of the lumen to the dry booster with the connecting device, wherein the lumen contacts the connecting device at a contact area; placing the dry booster, the connecting device, and the lumen into a chamber, wherein the chamber is at a pressure; introducing an antimicrobial vapor or gas into the chamber; causing the antimicrobial vapor or gas to penetrate the contact area and the lumen; and sterilizing the lumen. Preferably, the connecting device, at least in the contact area, is permeable to a germicide, and/or the surface of the connecting device in the contact area is textured or uneven. Preferably, the dry booster encloses an internal volume that is greater than the internal volume of the lumen. In one embodiment, the method further comprises reducing the pressure in the chamber, thereby at least partially evacuating the dry booster. In another embodiment, the method further comprises creating a higher pressure outside the dry booster than inside the dry booster; and flowing the antimicrobial vapor or gas from the chamber into the dry booster through the lumen. In another embodiment, the method further comprises reducing the pressure in the chamber after the flowing of the antimicrobial vapor or gas from the chamber into the dry booster through the lumen, thereby causing at least a portion of the antimicrobial vapor or gas in the dry booster to flow from the dry booster through the lumen and into the chamber.

In accordance with another aspect of the invention, an apparatus for sterilizing a lumen comprises a booster and a connecting device between the booster and the lumen, wherein the lumen contacts the connecting device at a contact area and wherein the connecting device comprises an uneven or textured surface in the contact area. Preferably, the connecting device is constructed from a material, at least in the contact area, that is permeable to the antimicrobial vapor or gas. In alternative preferred embodiments, the booster comprises a vessel containing an antimicrobial fluid, or the booster is a dry booster.

These and other embodiments are described in greater detail below.

BRIEF DESCRIPTION OF THE DRAWINGS

FIG. 7 is a schematic drawing of a pair of scissors having contact areas between the two parts of the scissors;

FIG. 8A is a sectional view of the contact area of the scissors of FIG. 7 with the scissors in a closed position, where both pieces of the scissors are textured, according to an embodiment of the invention;

FIG. 8B is a sectional view of the contact area of the scissors of FIG. 7 with the scissors in an open position, where both pieces of the scissors are textured, according to an embodiment of the invention;

FIG. 8C is a sectional view of the contact area of the scissors of FIG. 7 with the scissors in a closed position, where both pieces of the scissors are textured, according to an embodiment of the invention;

FIG. 8D is a sectional view of the contact area of the scissors of FIG. 7 in an open position, where both pieces of the scissors are textured, according to an embodiment of the invention;

DETAILED DESCRIPTION OF THE PREFERRED EMBODIMENT

Figure 1:
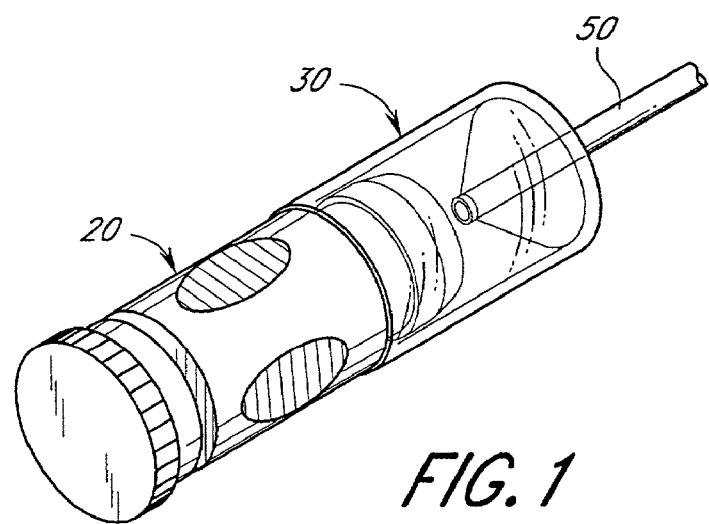
FIG. 1 is a perspective drawing of an assembled booster and adaptor with a lumen inserted in the opening of the adaptor.

The embodiments of the method and the apparatus of the present invention relate to the sterilization, disinfection, rinsing, drying, or cleaning of articles such as medical instruments having contact surfaces. Although certain embodiments of the apparatus and the method are discussed with the example of sterilizing areas of contact between a lumen and an adaptor, the apparatus and the method have broad applicability to a variety of forms of apparatus and methods. For example, the embodiments of the apparatus and the method of the present invention can be applied to disinfection, rinsing, or cleaning as well as sterilization.

The embodiments of the method and the apparatus apply to any situation in which there are contact areas between an article to be sterilized, disinfected, rinsed, dried, or cleaned and a device, part, adaptor, external housing, or connector. The embodiments of the method and the apparatus also apply to medical devices having two or more parts, where there are points of contact between the two parts. The embodiments of the method and the apparatus can be applied wherever contact areas exist on a device. The terms "sterilize", "sterilant", and other forms of this word throughout the specification and claims are to be construed broadly and are to be understood to include disinfection and other antimicrobial processes.

Embodiments of the method and the apparatus of the present invention are applicable to, for example, sterilization, rinsing, disinfection, drying, or cleaning of lumens or medical instruments having one or more lumens. The term "instruments having one or more lumens" as used herein applies to medical or surgical devices such as endoscopes, catheters, tubing, or similar instruments or articles having one or more internal lumens. In this embodiment of the device and the method of the present invention, antimicrobial fluid may be supplied directly to the lumen or interior of the tube of the instrument during the sterilization process. In general, the lumen is held by an adaptor which is connected to a source of antimicrobial agent or germicide. There are contact surfaces between the adaptor and the lumen.

To enhance the sterilization, rinsing, disinfection, or cleaning of the contact surfaces, one or a combination of the following properties may be utilized in the adaptor, medical device, or connector design and material selection: first, applying texture or uneven surfaces to the contact area so as to reduce surface contact and enhance axial diffusion of sterilant; second, constructing the adaptor, medical device, or connector, at least in the contact area, from a material which has minimal chemical and physical interaction with the sterilant; and third, using a material of construction, at least in the contact area, which is permeable to the sterilant so that the sterilizing agent can penetrate the material, enhancing radial diffusion of the sterilant.

The texture or uneven surfaces are designed so that more sterilant, disinfectant, rinsing fluid, or cleaning fluid can flow around the textured or the uneven surfaces on the adaptor or connector than flows though the material of the adaptor or connector.

Figure 2:
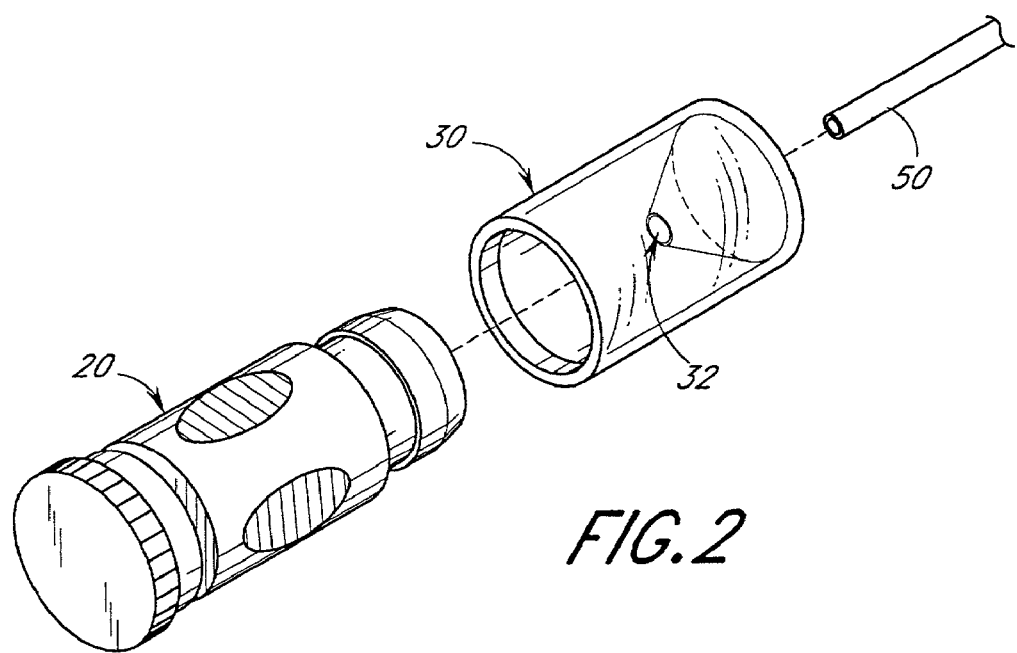
FIG. 2 is an exploded perspective drawing of the booster, adaptor, and lumen of FIG. 1.

FIGS. 1 and 2 illustrate an embodiment of an apparatus suitable for use in an embodiment of sterilizing or disinfecting a lumen. FIG. 1 shows the assembled apparatus, and FIG. 2 is an exploded view, showing the various parts of the apparatus. A booster 20 is attached to an adaptor 30. A lumen 50 is inserted into an opening 32 of the adaptor 30. The opening 32 is normally of slightly smaller diameter than the outer diameter of the lumen 50 so that there is a snug fit between the inside of the opening 32 and the outside of the lumen 50.

Two forms of the booster 20 are described in detail in col. 9 line 11 to col. 12, line 19 and FIGS. 5 to 13 of U.S. Pat. No. 5,580,530, hereby incorporated herein by reference in its entirety. Briefly, the booster 20 includes a vessel for containing hydrogen peroxide, a membrane wall capping the vessel containing the hydrogen peroxide, and an opener with a hollow spike which is used to breach the membrane wall, activating the booster so that the hydrogen peroxide can escape from the vessel. One form of the booster is shown as 100 on FIGS. 5 to 9 and an alternative form as 200 on FIGS. 10 and 11 of U.S. Pat. No. 5,580,530. Those skilled in the art will appreciate that a booster need not contain hydrogen peroxide and thus can be a dry booster, and that the adaptor described hereinbelow can be used with the booster, whether or not the booster contains an antimicrobial agent, e.g., hydrogen peroxide. Those skilled in the art will also appreciate that the booster and the adaptor can be parts of a single unit.

Figure 3A:
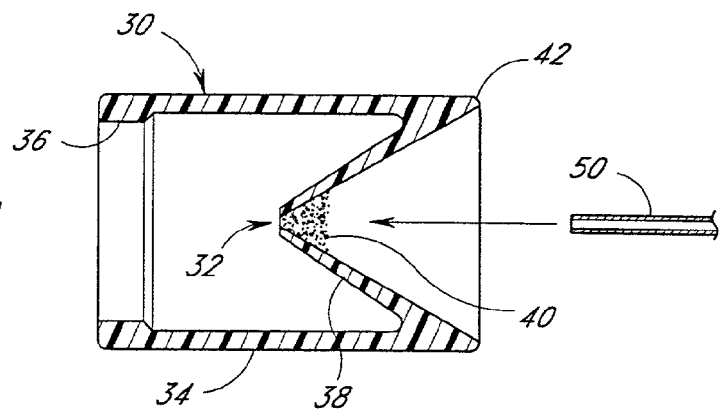
FIG. 3A is a sectional view of the adaptor and lumen, showing how the lumen fits into the opening of the adaptor.

The adaptor 30 is shown in more detail in FIG. 3A herein. The adaptor 30 includes a cylindrical tubular body 34, an inwardly facing annular flange 36 for firmly attaching the cylindrical tubular body 34 to the booster 20, a truncated cone 38, the opening 32, and texturing 40 on the contact surface of the truncated cone 38 surrounding the opening 32. The adaptor has one or a combination of the following properties.

First, texturing can be added to the contact surface. The texturing can take various forms such as ridges, concentric rings, uneven surfaces, projections having equal heights, projections with varying heights, etc. Whatever form of texturing is used, there can be a plurality of the ridges, rings, or projections of equal or varying heights. The height of the texturing varies and is generally related to the viscosity of the antimicrobial or cleaning fluid. The height of the texture varies from approximately 0.0001 millimeters to approximately 50 millimeters. The height of the texture for an antimicrobial fluid which is a gas will generally be less than for an antimicrobial fluid which is a liquid, because a gas has a lower viscosity than a liquid. Although the height of the texturing can be determined by one skilled in the art, in general, a height of approximately 0.001 millimeters to approximately 5 millimeters is preferred for an antimicrobial agent which is a gas. The height of the texturing for a gas is more preferably in the range of approximately 0.01 millimeters to approximately 2.0 millimeter, and most preferably in the range of approximately 0.1 millimeters to approximately 1.0 millimeters. The height of the texturing which is preferred for a liquid is normally in the range of approximately 0.01 to approximately 5 millimeters, depending on the viscosity of the liquid. The height of the texturing for a liquid is more preferably in the range of approximately 0.1 millimeters to approximately 4 millimeters, and most preferably in the range of approximately 0.2 to approximately 2 millimeters.

The texturing preferably extends to the inside of the opening 32, so that the area directly facing the lumen 50 as well as the outer surface of the truncated cone 38 surrounding the opening 32 is textured. The portion of the truncated cone 38 which is textured is preferably in the range of approximately 0.001 to 50 millimeters, more preferably in the range of approximately 0.01 millimeters to approximately 20 millimeters, and most preferably in the range of approximately 0.1 millimeters to approximately 10 millimeters, radically extending from the edge of the opening 32. The amount of the contact area to be covered with texture may depend on the length of the occluded area. The total length of the textured surface is preferably approximately 5 times the length of the occluded area, more preferably approximately 3 times the length of the occluded area, and most preferably approximately 1.5 times the length of the occluded area. The inwardly facing annular flange 36 fits into a shallow annular groove on the booster 20 when the adaptor 30 is fitted into place on the booster, firmly attaching the adaptor 30 to the booster 20. Those of skill in the art will appreciate that the dimensions of the truncated cone 38 and the opening 32 can be varied to accommodate various types of instruments to be sterilized.

Second, the material, at least in the contact area, preferably is compatible with the sterilant or sterilization agent, that is, has minimum chemical and physical interaction with the sterilant or sterilizing agent. Chemical interaction includes chemical reaction or catalytic decomposition of the sterilant. Physical interaction includes absorption or adsorption of the sterilant by the material. Third, the material, at least in the contact area, can be permeable to the sterilant so that the antimicrobial fluid can penetrate through the material.

Suitable materials for fabricating the adaptor, at least in the contact area, can include, but are not limited to, polyolefins (including thermoplastic elastomers), fluorinated and/or chlorinated polyolefins (including thermoplastic elastomers), fluorovinylidene, chlorovinylidene, liquid crystal polymers such as wholly aromatic polyester or polyesteramide, silicone rubber, fluorinated silicone rubber, or polyester. These materials can be mixed with one or more fillers which have minimum chemical/physical interactions with the chemical sterilant. Fillers can be added to enhance mechanical, electrical, or thermomechanical properties.

The following procedure may be used when sterilizing equipment with the booster 20 and the adaptor 30. An appropriately sized adaptor 30 is selected for the particular lumen 50 or other equipment to be sterilized. The adaptor 30 is attached to the booster 20, and the lumen 50 or other instrument to be sterilized is inserted into the opening 32. The booster 20 is activated by puncturing the membrane wall, and the hydrogen peroxide or other sterilizing agent is free to enter the adaptor 30 and the interior of the lumen 50 or instrument. In general practice, the activated booster 20, adaptor 30, and lumen 50 are placed into a sterilization chamber, the chamber is sealed, and the chamber is evacuated, preferably to a pressure of approximately 100 torr or less, more preferably to a pressure of approximately 50 torr or less, and most preferably to a pressure of approximately 10 torr or less. An antimicrobial fluid is then injected into the chamber, where it vaporizes and contacts the exposed surface of the equipment. For example, in the case of a lumen, it will be apparent from the foregoing to those skilled in the art that the lumen may be sterilized by the passage of antimicrobial vapor or gas from the chamber and through the lumen, and/or by the passage from a booster attached to the lumen, through the lumen and into the chamber, depending on the respective pressures in the booster and chamber. In either case, sterilization in the contact area takes place. Various factors known to those skilled in the art can be used to enhance sterilization such as heat, plasma, or high frequency radiation.

The hydrogen peroxide or other antimicrobial fluid in the booster 20 volatilizes when the chamber is evacuated. The germicide vapor enters the adaptor 30 and the lumen 50, sterilizing the interior of the lumen. The exterior of the lumen is sterilized by the antimicrobial agent which is injected into the chamber.

Figure 3B:
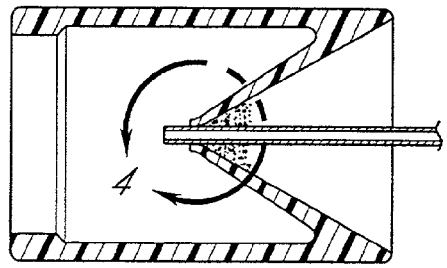
FIG. 3B is a sectional view of the adaptor and lumen, with the lumen inserted into the opening of the adaptor.

FIGS. 3A and 3B illustrate the use of the adaptor 30 with a lumen 50. One skilled in the art can appreciate that the size of the opening 32 on the adaptor 30 can be varied, depending on the size of the lumen 50 or other equipment connected to the adaptor 30. The body of the adaptor 30 can have shapes other than a cylinder, depending on the shape of the booster 20. For example, a rectangular adaptor 30 would be used if the booster 20 were rectangular. Similar modifications would be obvious to those skilled in the art.

Figure 4:
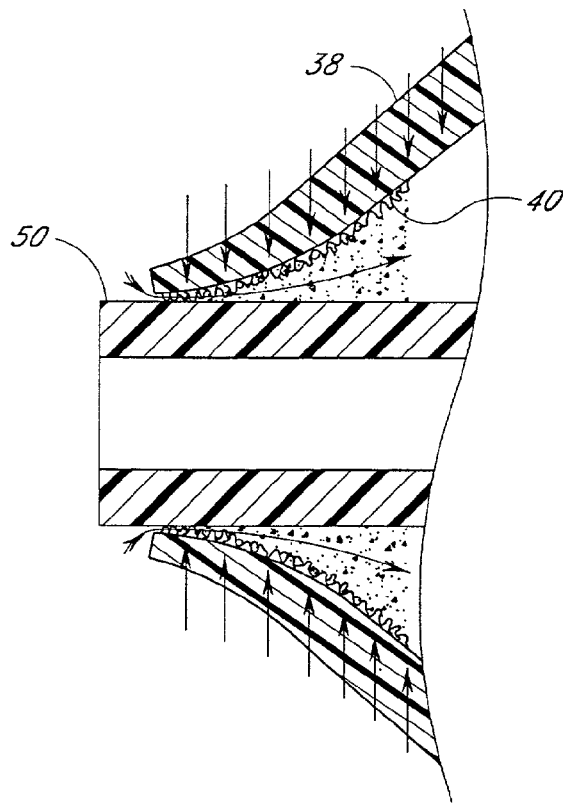
FIG. 4 is a blow-up of FIG. 3B showing a sectional view of the area of contact between the adaptor and the lumen, where the flow of sterilant vapor through the textured area of the adaptor and through the material of the adaptor is shown with arrows.

The adaptor 30 can have several features which make the sterilization of the lumen 50 even more effective than previous devices. Some of these features are illustrated in FIG. 4, which is a blowup of FIG. 3B, showing the area of contact between the lumen 50 and the adaptor 30. First, the areas of contact between the adaptor 30 and the lumen 50 or other medical device can be reduced by using textured surfaces on the adaptor 30. Thus, the opening 32 and the part of the truncated cone 38 which contact the lumen 50 can be textured, as shown in FIG. 4. Only the tips of the texturing devices remain as areas of contact between the adaptor 30 and the lumen 50. The contact area is far less than if the texturing were not present. In addition, there are small gaps between the ridges or "bumps" of the texturing which create an uneven surface. The uneven surface allows fluid penetration in both longitudinal and transverse directions. Therefore, the antimicrobial agent, rinsing fluid, or cleaning fluid can enter these gaps and reach areas which would otherwise be inaccessible.

Finally, if the material used to construct the adaptor 30 is permeable to the antimicrobial agent, typically hydrogen peroxide, peracetic acid, or chlorine dioxide, further enhancement of the sterilization effectiveness can be achieved. The antimicrobial agent can penetrate the adaptor 30 to reach any areas of contact between the adaptor 30 and the lumen 50 or other instrument which remain after the contact areas are minimized through surface texturing. FIG. 4 shows arrows illustrating the penetration of the sterilant vapor to the contact areas both through the gaps between the unevenness of the texturing and through the permeable material from which the adaptor 30 can be fabricated.

The effectiveness of penetration of the antimicrobial agent through the material of the adaptor 30 to the contact areas can be even further enhanced by making the adaptor 30 thinner in the contact areas than in the remainder of the adaptor 30. For example, in FIGS. 3A and 4, the wall thickness of the truncated cone 38 of the adaptor 30 decreases from the outer end 42 to the opening 32. The portion of the truncated cone 38 which is in contact with the lumen 50 is the thinnest part of the truncated cone 38, and the antimicrobial agent can penetrate to the contact area between the adaptor 30 and the lumen 50 more effectively than if the adaptor 30 in this area were thicker. Making the adaptor 30 thinner in the contact areas than in the remainder of the adaptor 30 is a way to further enhance the penetration of the antimicrobial agent through the material of the adaptor 30 into the contact area. Although this is a preferred embodiment, it is not a required feature.

By using one or a combination of these features in the adaptor 30, the contact area can be adapted so that the antimicrobial agent can penetrate the areas of contact between the adaptor 30 and the lumen 50 more effectively than in previous designs. These features include: applying texture or uneven surfaces to the contact area so as to reduce surface contact and enhance bidirectional diffusion of sterilant; using a material which has minimal chemical and physical interaction with the sterilant; and forming the adaptor 30 from a material that is permeable to the sterilant so that the sterilizing agent can penetrate the material.

The embodiments of the method and the apparatus of the present invention can be used whenever there are areas of contact between an article to be sterilized through sterilization and a connecting device for the article. Often, the connecting device will have an aperture through which the article is inserted. Those skilled in the art will appreciate that the various adaptors described herein are examples of connecting devices. There are areas of contact between the aperture of the connecting device and the article to be sterilized. The article to be sterilized can include a lumen, rod, or other device. The methods of the present invention can be used in the connecting device and/or the article to be sterilized. These methods include the use of texturing on the areas of the connecting device which contact the device to be sterilized in order to reduce the contact area between the article and the connecting device. Second, the connecting device can be made of a material which is permeable to the antimicrobial agent so that any remaining contact surfaces can be sterilized by penetration of the antimicrobial agent through the material of the adaptor. Those skilled in the art are aware that silicone is one of the polymers which is most permeable to gases and vapors. Third, the selected material can be a material which has minimal physical and chemical interaction with the antimicrobial agent. Ways to optimize these design modifications will be apparent to those skilled in the art. Generally, the height of the texturing is selected to match the viscosity of the sterilant or sterilizing agent so that more sterilant or cleaning fluid flows around the texturing than through the material of the adaptor, connector, or device. The embodiments of the method and the apparatus are applicable to sterilization, rinsing, disinfection, and cleaning of devices with contact areas.

Embodiments of the method and the apparatus of the present invention can also be used to enhance the penetration of antimicrobial agents, disinfection fluids, rinsing fluids, or cleaning fluids to contact areas within a medical device during cleaning, rinsing, disinfecting, and sterilization processes. The embodiments of the method and the apparatus have broad applicability.

Figure 5:
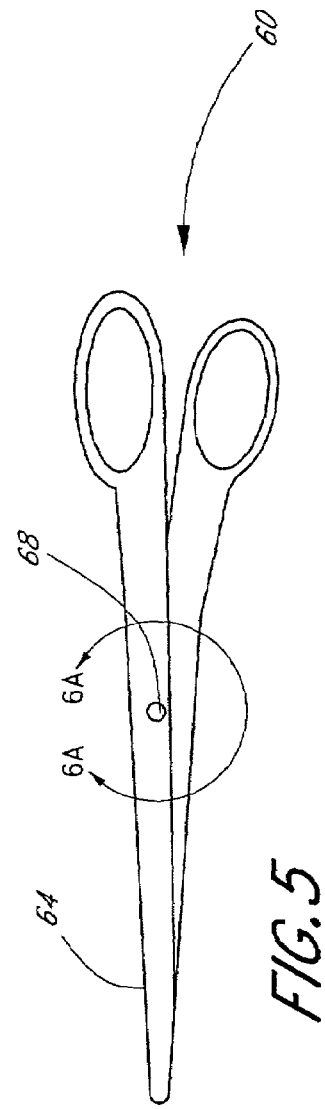
FIG. 5 is a schematic drawing of a pair of scissors having contact areas between the two parts of the scissors.

Often a medical device is made of two or more pieces. There are likely to be contact areas between the pieces from which the medical device is formed. FIG. 5 shows one example of a medical device made up of two or more pieces and having contact areas, a pair of scissors 60. The pair of scissors 60 is made up of two cutting blades 64 joined at the center by a pin 68 which forms a pivot point. The portion of the cutting blades 64 in the area of the pin 68 form a contact area which is difficult to clean, disinfect, rinse, or sterilize.

Figure 6B:
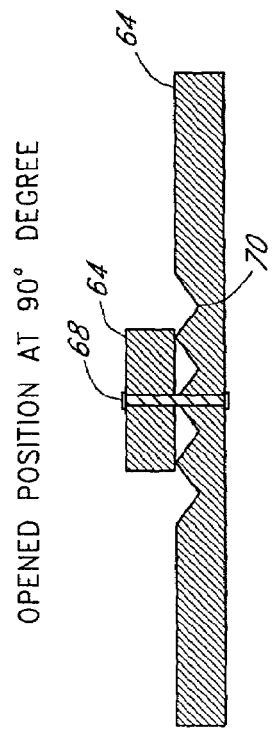
FIG. 6B is a sectional view of the contact area of the scissors of FIG. 5 with the scissors in an open position, where one of the pieces making up the scissors is textured, according to an embodiment of the invention.
Figure 6A:
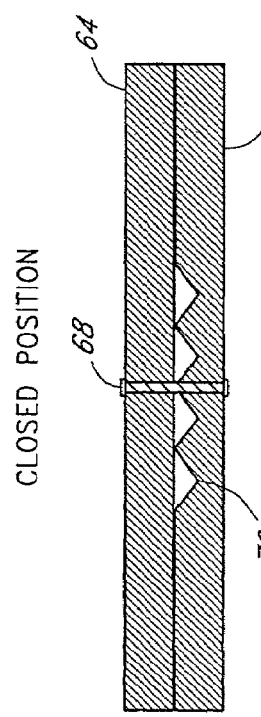
FIG. 6A is a sectional view of the contact area of the scissors of FIG. 5 with the scissors in a closed position, where one of the pieces making up the scissors is textured, according to an embodiment of the invention.

FIG. 6A shows a cross section of the two blades 64 and the pin 68 of the scissors 60 of FIG. 5, where the pair of scissors 60 is in a closed position. In the embodiment shown in FIG. 6A, a plurality of grooves 70 are present in the contact area around the pin 68 in one of the blades 64. The grooves 70 allow cleaning fluid, disinfecting fluid, rinsing fluid, or germicide to flow into the contact area, cleaning, disinfecting, rinsing, or sterilizing the contact area. FIG. 6B shows the two blades 64 of the scissors 60 in an open position. The contact area between the two blades 64 when the pair of scissors 60 is in the open position shown in FIG. 6B is less than the contact area between the two blades 64 when the scissors 60 are in the closed position, as shown in FIG. 6A. The grooves 70 allow cleaning fluid, disinfectant, rinsing fluid, or sterilant to flow into the contact areas, whether the pair of scissors 60 is in the open position or in the closed position. Because the contact area of the pair of scissors 60 is reduced when the pair is scissors 60 is in the open position, it is preferred that the cleaning, disinfecting, rinsing, or sterilizing be performed when the pair of scissors 60 is in the open position, though the grooves 70 or other texturing devices in the contact area increase the effectiveness of the cleaning, disinfecting, rinsing, or sterilizing whether the pair of scissors 60 is in the open position or in the closed position.

FIG. 8A shows a cross section of an embodiment of the scissors 60 of FIG. 7 in which both blades 64 making up the scissors 60 have a plurality of grooves 70 in the contact area in the region of the pin 68 which joins the two blades 64 at a pivot point. In FIG. 8A, the scissors 60 are in a closed position. FIG. 8B shows a cross section of the scissors 60 of FIG. 7 in an open position. The amount of contact area between the blades 64 in the open position shown in FIG. 8B is reduced from the contact area between the blades 64 in the closed position shown in FIG. 8A. Cleaning fluid, disinfectant, rinsing fluid, or germicide can flow through the grooves 70 into the contact area, cleaning, disinfecting, rinsing, or sterilizing the remaining contact area.

In the embodiment shown in FIG. 8A, the grooves 70 in the two blades 64 are in a staggered arrangement, that is, a point 72 of the groove 70 in an upper blade 64 is aligned with a valley 74 in a lower blade 64. As seen in FIG. 8A, there are no points of contact between the top blade 64 and the bottom blade 64 in the portion of blades 64 with grooves 70 when the blades 64 are in the closed position in the embodiment where the grooves 70 in the two blades 64 are in a staggered arrangement.

FIGS. 8C and 8D show an alternate embodiment of the scissors 60 in which the points 72 in the upper blade 64 are aligned with the points 72 in the lower blade 64, and the valleys 74 in the upper blade 64 are aligned with the valleys 74 in the lower blade 64.

Figure 10:
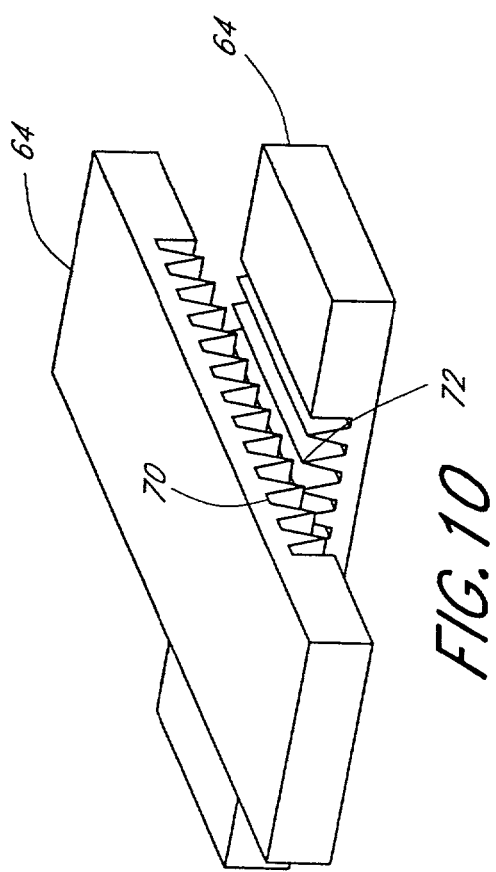
FIG. 10 is a perspective view of a contact area between two parts of a medical device, where both parts are textured and where the two parts are in an open position.
Figure 9:
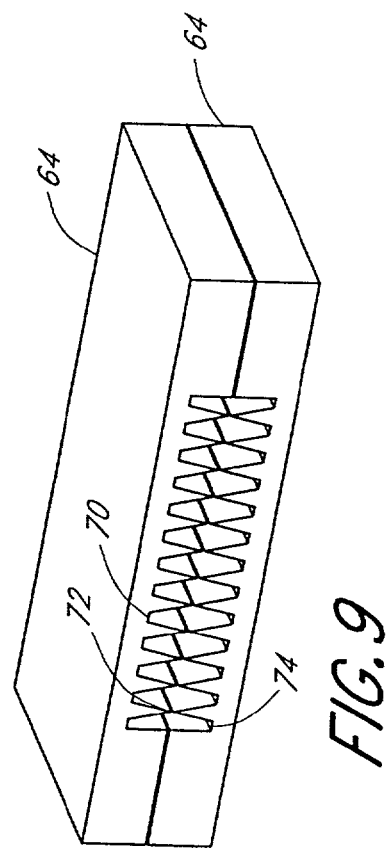
FIG. 9 is a perspective view of a contact area between two parts of a medical device, where both parts are textured and where the two parts are in a closed position.

FIGS. 9 and 10 show two alternative perspective views of the blades 64 of the embodiments shown in FIGS. 8C and 8D. The points 72 of the grooves 70 in a the top blade 70 are aligned with the points 72 of the grooves 70 in the bottom blade 70. In the closed position shown in FIG. 9, the contact areas between the two blades 64 are a plurality of parallel lines formed by the contact between the points 72 in the upper blade 64 and the points 72 in the lower blade 64.

FIG. 10 shows the two blades 64 in an open position. When the blades 64 are in the open position shown in FIG. 10, the areas of contact between the points 72 of the grooves 70 in the top blade 64 and the points 72 of the grooves 70 on the lower blade 64 are a plurality of points. The grooves 70 on the blades 64 thus greatly reduce the amount of contact area between the two blades 64, whether the blades 64 are in an open position or in a closed position. Because the contact areas between the blades 64 are a plurality of points when the blades 64 are in an open position versus a series of lines when the blades 64 are in a closed position, it is preferred that the blades 64 be in an open position when the cleaning, disinfecting, rinsing, or sterilization is performed. Regardless of whether the blades 64 are in an open position or in a closed position, cleaning fluid, rinsing fluid, disinfectant, or germicide can flow through the grooves 70 to clean, rinse, disinfect, or sterilize the blades 64, even the contact areas between the blades 64.

Figure 12B:
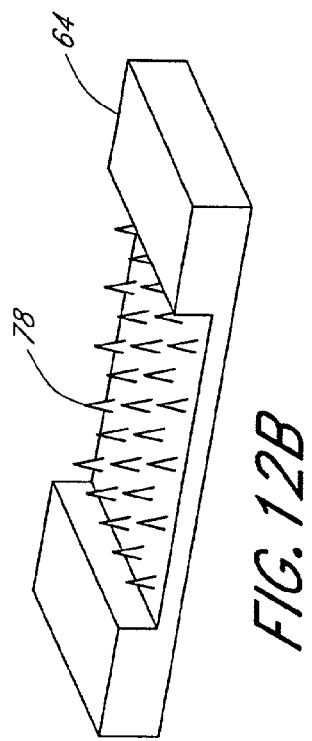
FIG. 12B is a perspective view texturing according to an embodiment of the invention, where the texturing is in the form of projections placed in rows on the contact surface.
Figure 11:
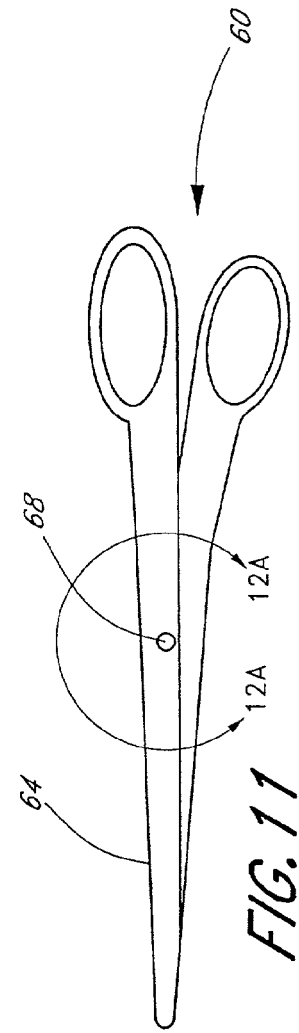
FIG. 11 is a schematic drawing of a pair of scissors having contact areas between the two parts of the scissors.
Figure 12A:
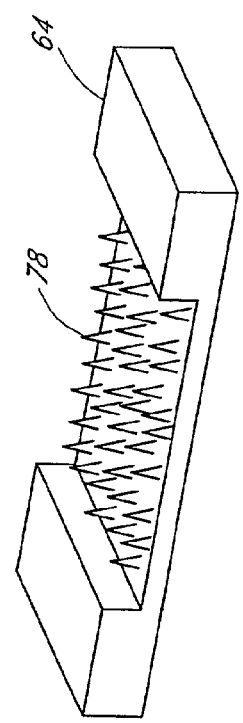
FIG. 12A is a perspective view of texturing according to an embodiment of the invention, where the texturing is in the form of projections placed randomly on the contact surface.
Figure 12C:
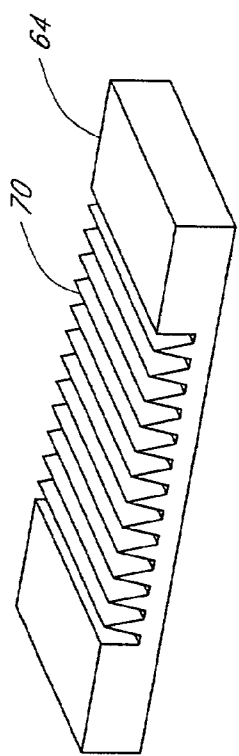
FIG. 12C is a perspective view of texturing according to an embodiment of the invention, where the texturing is in the form of grooves.

FIGS. 12A, 12B, and 12C show various embodiments of texturing that may be used to reduce the contact area between two or more parts of a medical device, for example the pair of scissors 60 shown in FIG. 11. In the embodiment shown in FIG. 12A, the texturing on the contact surface is in the form of a plurality of projections 78 in random positions on the contact surface. In the embodiment shown in FIG. 12B, the texturing on the contact surface is in the form of projections 78 aligned in regular rows on the contact surface. In the embodiment shown in FIG. 12C, the texturing on the contact surface is in the form of grooves 70. Although the projections 78 and grooves 70 of FIGS. 12A, 12B, and 12C are shown as having equal heights, in other embodiments, the projections 78 and grooves 70 can have unequal heights. Other forms of texturing on the contact surfaces are suitable for use in the embodiments of the apparatus and the method of the invention, and the embodiments of texturing shown in FIGS. 12A, 12B and 12C are not meant to be limiting.

In other embodiments, the plurality of projections 78 can have the shapes of points, lines, or a combination of points and lines. In some embodiments, the plurality of projections 78 can be combinations of the random arrangement of projections 78 of FIG. 12A, the arrangement of projections 78 in rows of FIG. 12B, and/or the grooves 70 of FIG. 12C.

The plurality of projections or texturing on the contact areas between the two or more parts surfaces provide a pathway for the cleaning fluid, rinsing fluid, scrubbing fluid, or germicide to contact the contact surfaces. The projections 78 are adapted so that when fluid is applied to the medical device, more fluid flows around the projections or texturing than through the material of which the medical device is made. The fluids can be liquid, vapor, or gas.

When medical devices are made of two or more parts with contact areas between the parts, the parts are often movable. As shown in the example of the scissors 60 of FIGS. 5, 7, and 11, the two parts are often movable around a pivot. The pivot in the example of the scissors 60 of FIGS. 5, 7, and 11 is the pin 68.

The medical device with two or more parts can be made from a variety of materials such as metal or nonmetals, including, but not limited to, TEFLON™, a tradename for polytetrafluoroethylene, nylon, a generic name for polyamide, polyolefins (including polyethylene, polypropylene, and thermoplastic elastomers), stainless steel, titanium alloy, aluminum alloy, nickel-chrome alloy, liquid crystal polymer, polyester, silicon rubbers, and styrenic thermoplastic, including thermoplastic elastomers. Further, the materials from which the two or more parts are formed need not be the same. For example, one part of the medical device can be made of metal and another part from a non-metal.

The medical device with two or more parts can be disposable or reusable. The contact areas on the medical device can be due to a joint, a hinge, a box lock, or a mated surface. Devices with hinged surfaces include scissors, forceps, and clips. Typical medical devices with two or more parts having contact surfaces include scissors, forceps, holders, hemostats, or rongeurs. The embodiments of the apparatus and the method of the present invention can also be applied to luer locks, connector housings, or any connectors that join two devices, for example, venting caps for flexible endoscopes or connectors on flexible endoscope heads for all-channel irrigators.

Fluids which may be used with the embodiments of the apparatus and the method of the invention include cleaning fluids, rinsing fluids, scrubbing fluids, or germicides. The germicide may be a liquid, a gas, or a vapor. The germicide can be a disinfectant or a sterilant.

One or more of the pieces forming the medical device can incorporate the features of the embodiments of the method or the apparatus of the present invention to enhance the penetration of the fluid to the contact areas. These features include the use of texturing or uneven surfaces on one or more of the pieces forming the medical device in the contact areas between the two or more pieces. The texturing helps to reduce the contact area. between the pieces forming the medical device. Second, one or more of the pieces forming the medical device, at least in the contact area, can be made of a material which is permeable to the antimicrobial agent. Third, the material selected to form one or more of the pieces forming the medical device, at least in the contact area, can be a material which has minimal physical and chemical interaction with the antimicrobial agent. Any one or a combination of these features can be used to enhance the penetration of the cleaning fluid, rinsing fluid, scrubbing fluid, disinfecting fluid, or sterilizing fluid to the contact areas between the two or more pieces forming a medical device.

The antimicrobials used with the embodiments of the method and devices of the various embodiments of the present invention include solutions of glutaraldehyde, hydrogen peroxide, chlorine dioxide, peracetic acid, or other antimicrobials, either in a pure form or in an inert medium. Although high concentrations of the antimicrobial agents are more effective, material compatibility and handling problems may arise at high concentrations.

When a medical device with two or more parts having embodiments of the apparatus of the present invention is cleaned, rinsed, scrubbed, disinfected, or sterilized with a liquid, the medical device is contacted with the cleaning, rinsing, scrubbing, disinfecting, or sterilizing liquid. Advantageously, the medical device is contacted with the liquid in a vessel. If the contacting is in a vessel, the liquid may be circulated in the vessel. The cleaning, rinsing, scrubbing, disinfecting, or sterilizing liquid penetrates to the contact areas of the medical device. More liquid flows around the plurality of projections on the contact surface than through the material of the medical device, thus cleaning, rinsing, scrubbing, disinfecting, or sterilizing the medical device and the contact areas between the two or more parts of the medical device. The effectiveness of the cleaning, rinsing, scrubbing, disinfecting, or sterilizing can be enhanced even further by moving the two or more parts of the medical device during the cleaning, rinsing, scrubbing, disinfecting, or sterilizing. Moving the parts of the medical device changes the contact areas between the two or more parts.

If the medical device with two or more parts having embodiments of the apparatus of the present invention is to be cleaned, rinsed, scrubbed, disinfected, or sterilized with a vapor or gas, the medical device is placed in a chamber, the chamber is sealed, and the cleaning, rinsing, scrubbing, disinfecting, or sterilizing fluid is introduced into the chamber. The pressure in the chamber may optionally be reduced to vaporize the fluid. More fluid flows around the projections on the contact area than flows though the material of the medical device to clean, rinse, scrub, disinfect, or sterilize the contact area between the two or more parts of the medical device. Contacting the medical device also cleans, rinses, scrubs, disinfects, or sterilizes the remainder of the medical device which does not have contact areas.

In a preferred embodiment, the method and device of the present invention relate to the sterilization of articles, such as medical devices containing long, narrow lumens, using a dry booster. The medical devices are devices such as endoscopes, catheters, tubing, or other instruments having lumens, where the device is preferably sterilized before use. Typical applications include surgery, medical applications, and the agricultural and fermentation industries.

The preferred embodiment has particular advantage in applications for sterilizing lumens having internal diameters of 3 mm or less or having a length of 27 cm or more, though the method is also applicable to lumens having wider diameters or shorter lengths. The germicides used with the method of the present invention are varied. Suitable germicides include, without limitation, glutaraldehyde, hydrogen peroxide, chlorine dioxide, or ethylene oxide. Unlike the other methods which use boosters, the germicide is not limited to being liquid at atmospheric pressure and a vapor at the temperature and pressure utilized in the sterilization process. Both vapor and liquid processes are applicable to the embodiments of the present method utilizing a dry booster. With the use of the device of the present invention, antimicrobial vapor is drawn through the lumen or interior of the tube of the instrument during the vapor sterilization process without the need to supply a separate vial of liquid germicide on the end of the lumen, as with the wet boosters previously used.

The procedure for vapor sterilization using a dry booster is generally as follows. The article to be sterilized is placed into the sterilization chamber, the chamber is sealed, and the chamber is evacuated to a pressure of less than about 50 torr, more preferably to 20 torr or less. An antimicrobial solution is then injected into the chamber, where it vaporizes and contacts the exposed surfaces of the article. The time necessary for total kill of specific microbial agents varies with the type and concentration of antimicrobials present and with the degree of exposure to the microbial agent. Microbials in cracks, crevices, mating surfaces, or diffusion restricted areas are somewhat protected from the antimicrobial agent and require more time for total kill than microbials on the external surface of the article. Heat or high frequency radiation such as plasma may be used to increase the effectiveness of the antimicrobial and its penetration into remote areas of the instrument.

The device of the preferred embodiment comprises a vessel and a means for connecting the vessel directly to the lumen or the end of the tube of the article to be sterilized. Unlike the prior vessels, the vessel of the dry booster of the present invention does not contain antimicrobial solution. The prior boosters contained antimicrobial liquid which vaporized when exposed to vacuum. The antimicrobial vapor traveled from the vessel into the lumen.

In the preferred embodiment, the vessel attached to the lumen does not contain antimicrobial liquid. When the chamber is evacuated, the vessel, the lumen, and the means for connecting the vessel to the lumen are also at least partially evacuated. When antimicrobial vapor is injected into the chamber, the antimicrobial vapor is drawn into the lumen because of the vacuum from the large evacuated volume of the vessel attached to the lumen. Those skilled in the art will appreciate that injection of the antimicrobial vapor is injected into the chamber causes the pressure in the chamber to be higher than in the booster, thereby enhancing flow of the antimicrobial vapor from the chamber into the dry booster through the lumen. Unlike the prior boosters, the antimicrobial vapor is drawn inward into the vessel from the sterilization chamber rather than being drawn out of the vessel into the sterilization chamber. Although in both cases, the antimicrobial vapor is drawn through the lumen, with the dry booster of the present invention, there is no need to have a vessel containing antimicrobial liquid. Those skilled in the art will appreciate that the pressure in the chamber can be reduced after the flowing of the antimicrobial vapor or gas from the chamber in the dry booster through the lumen (such as by venting the chamber to the atmosphere), causing at least a portion of the antimicrobial vapor or gas in the dry booster to flow from the dry booster through the lumen and into the chamber.

Figure 13:
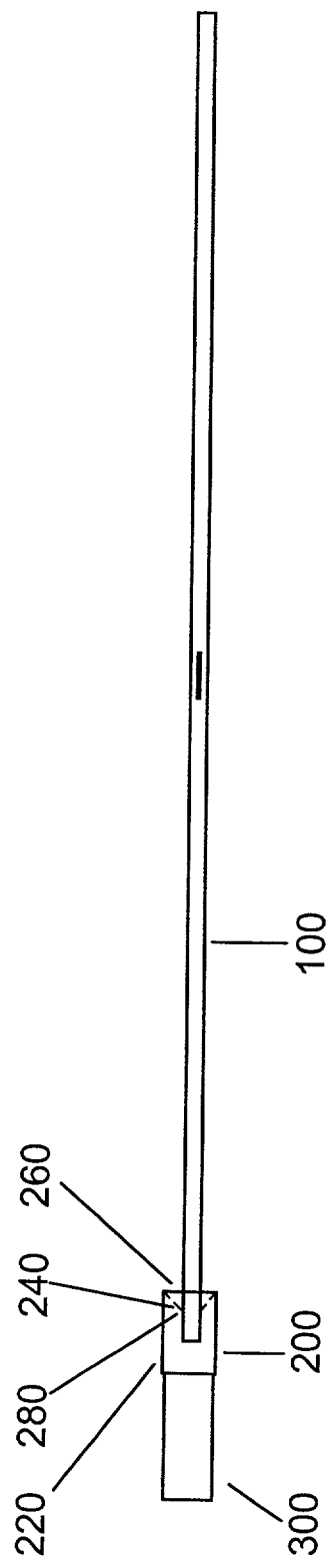
FIG. 13 is a schematic diagram of a lumen attached to an adaptor which is connected to a vessel according to a preferred embodiment of the invention.

A form of "dry booster" suitable for use in the method of the present invention is shown in FIG. 13. A lumen 100 is attached by a first end to an adaptor 200. The second end of the lumen is open to the interior of the sterilization chamber. The adaptor 200 shown in FIG. 13 is described in U.S. Pat. No. 5,580,530, herein incorporated by reference. The adaptor is shown as item 170 in FIG. 6 of U.S. Pat. No. 5,580,530. The adaptor 200 comprises a cylindrical tubular body 220 formed of a soft thermoplastic elastomer, such as Schafer, GmbH THEKA-FLEX, S 2030M or silicone. Those skilled in the art will appreciate that the use of these materials is not limited to the adaptor 200, and that other connecting devices may also comprise these materials. For the adaptor 200 in FIG. 13, a truncated cone 240 extends inwardly, proximally, from a distal end 260 of the adaptor body and terminates in a central opening 280. The lumen 100 is inserted into the central opening 280 of the adaptor 200. The end of the adaptor 200 not having the truncated cone 240 is attached to a vial 300.

The vial 300 is a receptacle of any shape which encloses a substantial empty volume. Although the vial 300 of FIG. 13 is a cylinder, other shapes are suitable, including round, rectangular, square, elliptical, or any other suitable shape. All that is important is that the vial 300 and the adaptor 200 enclose a substantial volume of space which can be evacuated when the vial 300 is attached to the adaptor 200 and the lumen 100.

Other forms of adaptor 200 and vial 300 are suitable for use with the method of the invention, including the various adaptors described herein. For example, those skilled in the art are aware that silicone is one of the polymers which is most permeable to gases and vapors, and thus also realize that an antimicrobial gas or vapor can penetrate the contact area between the adaptor and lumen when the adaptor, at least in the contact area, comprises a material such as silicone. All that is necessary is that the adaptor 200 provide a fluid link between the lumen 100 and the vial 300 and that the vial 300 and adaptor 200 enclose sufficient volume relative to the volume of the lumen 100 to be sterilized. As will be shown below, the required ratio of the volume of the vial 300 and adaptor 200 relative to the volume of the lumen 100 depend on the process conditions in the sterilization. Some suitable forms of adaptor 200 and vial 300 for use in the method of the present invention are shown, for example, in FIGS. 1, 2, 2A, 3, and 3A of U.S. Pat. No. 5,580,530. The embodiments of the adaptor shown in U.S. Pat. No. 5,580,530 include an expandable sheath, a bushing comprising a series of rings of inwardly extending plastic flaps, a bushing with an aperture for attaching disposable cartridges, a drawstring on a pouch, and a "zip-lock" closure on a pouch. These forms of the adaptor 200 are illustrative only, and the method of the invention is not limited to these forms of adaptor 200.

The vial 300 can comprise any three dimensional container preferably of semi-rigid or rigid material, having an opening therein. The vial 300 may be made of, e.g., polyethylene, polypropylene, glass, or any other material which is compatible with the antimicrobial vapor. In the embodiments shown in FIGS. 3 and 3A of U.S. Pat. No. 5,580,530, the vial 300 comprises a pouch. In the embodiments shown in FIGS. 1 and 2A of U.S. Pat. No. 5,580,530, the vial 300 comprises a vial. Any shape of vial 300 may be used in the method of the present invention. The major restriction on the vial 300 is that the vial 300 and adaptor 200 together have a volume larger than the volume of the lumen 100. Those skilled in the art will appreciate that, when the adaptor 200 is not present, the vial 300 should have an internal volume that is greater than the internal volume of the lumen. The required ratio of the volume of the vial 300 and adaptor 200 relative to the lumen 100 depend on the process conditions, and the required ratios will be described in the Examples below.

Experiments were performed to compare the sterilization efficiency with and without a dry booster. In both sets of experiments, a biological indicator of $1.6 \times 10^6$ *Bacillus stearothermophilus* spores on a stainless steel wire was placed in the center of a stainless steel lumen 100. For the experiments in Example 1, both ends of the lumen 100 were left open. For the experiments with the dry booster in Example 2, the apparatus shown in FIG. 13 was used. A first end of the lumen 100 was attached to a first end of the adaptor 200 described in FIG. 6 of U.S. Pat. No. 5,580,530. The second end of the adaptor 200 was attached to an empty polyethylene scintillation vial 300 with 17 mm outside diameter. Vials 300 having varying lengths were tested to provide a range of volumes of adaptor 200 and vial 300 relative to the volume of the lumen 100. The sterilization results for the lumen without the dry booster are given in Example 1. The sterilization results for the experiments when the dry booster was attached to the lumen are given in Example 2.

EXAMPLE 1

Sterilization Results with no Dry Booster on the Lumen

In Example 1, biological indicators of $1.6 \times 10^6$ B. stearothermophilus spores were placed in the center of lumens of various lengths. The lumens were placed in a 72.5-liter STERRAD 50 sterilizer with a standard STERRAD 50 load double wrapped with CSR wraps. The chamber was evacuated to 0.4 torr, and 740 mg of 59 weight % hydrogen peroxide were injected for 5 minutes to provide 6 mg/L of hydrogen peroxide vapor in the chamber. After 5 minutes of injection and diffusion, the chamber was vented to atmospheric pressure, the lumens were removed, and the sterility results of the biological indicators were determined. The results are shown in Table 1 below.

TABLE 1

Sterility Results From Tests with No Dry Booster
(No. of Positives/No. of Samples)

| Lumen Size | Sterility Results |
| --- | --- |
| 1 mm × 250 mm | 0/3 |
| 1 mm × 300 mm | 0/3 |
| 1 mm × 350 mm | 0/3 |
| 1 mm × 400 mm | 1/2 |
| 1 mm × 450 mm | 3/3 |
| 1 mm × 500 mm | 2/2 |

As shown by the results in Table 1 above, under the test conditions, the interiors of the 1 mm ID lumens longer than 350 mm were not sterilized by exposure to hydrogen peroxide vapor.

In Example 2, a "dry booster" comprising an adaptor 200 and a vial 300 containing no liquid sterilant was attached to one end of the lumen 100. All of the other test conditions were the same as in Example 1. The results in Example 2 demonstrate the improvement in sterilization efficiency of the interiors of long lumens when the "dry booster" according to an embodiment of the method of the present invention was attached to the end of the lumen 100 to be sterilized.

EXAMPLE 2

Sterilization of Lumens with a "Dry Booster"

In the experiments of Example 2, one end of an adaptor 200 as described in U.S. Pat. No. 5,580,530 was attached to an end of a 1 mm×400 mm stainless steel lumen to be sterilized. A biological indicator as described in Example 1 was placed in the center of each lumen. The second end of the adaptor 200 was attached to a 17 mm ID polyethylene scintillation vial 300 having varying lengths and therefore varying volumes, as shown in FIG. 13. The lumens 100 with the attached boosters comprising an adaptor 200 and vial 300 were exposed to hydrogen peroxide vapor under the conditions described in Example 1, the chamber was vented, and the sterility tests were measured. The results are shown in Table 2 below.

TABLE 2

Sterility Results From Tests with a Dry Booster
(No. of Positives/No. of Samples)

| Ratio of Dry Booster Volume/Internal Volume of 1 mm × 400 mm Lumen | Sterility Results |
| --- | --- |
| 20:1 | 0/3 |
| 15:1 | 0/3 |
| 14:1 | 0/3 |
| 13:1 | 0/3 |
| 12:1 | 0/3 |
| 11:1 | 1/3 |
| 10:1 | 1/3 |
| 5:1 | 1/2 |

A 1 mm×400 mm stainless steel lumen was chosen for the tests in Example 2, because the 400 mm lumen was the shortest lumen which was not sterilized without the need for a dry booster in Example 1.

There are two conclusions which can be drawn from the results shown in Table 2. First, use of a "dry booster" can enhance the sterilization of the interior of lumens. The interior of the 1×400 mm lumen in Example 1 was not sterilized. By contrast, the interior of the 1×400 mm lumen was sterilized in the majority of the examples shown in Example 2, where a dry booster was attached to the end of the 1×400 mm lumen.

Second, the interior of the 1×400 mm lumen was not sterilized unless the ratio of the dry booster volume (the volume of the adaptor 20 and the vial 30) was at least 12 times as large as the internal volume of the 1 mm×400 mm stainless steel lumen. In cases where the ratio of the volume was less than 12:1, not all of the samples were sterilized. A volume of dry booster to the volume of the lumen of 12:1 or more is therefore required for the dry booster to be effective in enhancing the sterilization of the interior of the lumen, under the conditions of Example 2.

The comparative results from Examples 1 and 2 demonstrate the improvement in sterilization efficiency for long lumens when a dry booster having a volume of 12 or more times the volume of the lumen is attached to the end of the lumen to be sterilized and the chamber was evacuated to a pressure of 0.4 torr before the hydrogen peroxide was injected into the chamber.

A series of experiments were performed to determine the sterilization efficiency at various initial vacuum pressures. The length of time for which the vacuum was maintained before injection of the hydrogen peroxide was also varied. The effects of pressure and length of the evacuation time are shown in Example 3 below.

EXAMPLE 3

Effects of Varying Evacuation Pressure and Evacuation Time

A plurality of 1 mm×500 mm stainless steel lumens 100, each containing a biological indicator, were placed in a 72.5 liter sterilization chamber as in Example 1. Dry boosters having various volumes were attached to the ends of certain of the lumens, as shown in FIG. 13. The remainder of the lumens were placed into the chamber without a dry booster. The chamber was evacuated to a pressure of either 0.4 torr or 0.1 torr and was maintained at the pressure of 0.4 torr or 0.1 torr for a time period of between 0 and 20 minutes, as noted in Table 3 below. A total of 740 mg of 59 weight % hydrogen peroxide was injected for 5 minutes to provide 6 mg/L of hydrogen peroxide vapor in the chamber. After 5 minutes of injection and diffusion, the chamber was vented to atmospheric pressure, the lumens were removed, and the sterility results of the biological indicators were determined. The results are shown in Table 3 below.

TABLE 3

Dependence of Sterility Results on Evacuation Pressure, Evacuation Time, Presence of a Dry Booster, and Volume Ratio of Dry Booster to Lumen (No. of Positives/No. of Samples)

| Evacuation Conditions | | Sterility Results | | | |
|---|---|---|---|---|---|
| | | No | Volume Ratio of Dry Booster to Lumen | | |
| Evacuation Pressure | Evacuation Time | Booster | 10:1 | 5:1 | 3:1 |
| 0.4 torr | 0 minutes | 2/2 | 1/2 | 2/2 | — |
| 0.4 torr | 5 minutes | 2/2 | 0/2 | 2/2 | — |
| 0.1 torr | 0 minutes | 2/2 | 0/2 | 2/2 | — |
| 0.1 torr | 10 minutes | 2/2 | 0/2 | 1/2 | 2/2 |
| 0.1 torr | 20 minutes | 1/2 | — | 0/2 | 0/2 |

There are several conclusions that can be drawn from the data in Table 3. First, the sterilization efficiency of the lumen improves with lower evacuation pressures and longer evacuation times. For example, sterilization with a 10:1 booster was not effective at 0.4 torr with no vacuum hold time. The sterilization was effective when the vacuum was maintained at a pressure of 0.4 torr for 5 minutes, however. Similarly, sterilization with a 10:1 booster was not effective with a sterilization pressure of 0.4 torr with no hold time, but the sterilization was effective at a pressure of 0.1 torr with no hold time.

Second, the sterilization efficiency with a dry booster was at least as high as with no dry booster in all cases.

Third, the sterilization efficiency improved with higher ratios of dry booster volume: lumen volume. All but 1 of the coupons were sterilized when a dry booster with 10 times the volume of the lumen was used. The sterilization efficiency steadily decreased as the ratio of the dry booster volume to the volume of the lumen decreased from a ratio of 10:1 to 5:1 and even further when the ratio decreased to 3:1.

Fourth, the ratio of the volume of the dry booster to volume of the lumen required to sterilize the interior of the lumen can be decreased by using lower evacuation pressures and longer evacuation times. In Example 2, ratios of dry booster volume/lumen volume of 12:1 were required to sterilize the interior of the lumens with evacuation pressures of 0.4 torr with no hold on the evacuation time.

In Example 3, the interior of the lumens could be sterilized when the volume of the dry booster (adaptor and vial):volume of lumen was 5:1 or even 3:1 when the pressure was reduced to 0.1 torr and the chamber was evacuated to 0.1 torr for 20 minutes. Evacuating the chamber to lower pressures for longer times therefore allows dry boosters with lower volumes relative to the volume of the lumen to be effective in sterilizing the lumens.

It is believed that the reason that the sterilization efficiency improves with longer evacuation times is because the increased exposure time to the vacuum removes more moisture from the lumen. When less moisture is present, more hydrogen peroxide can be drawn into the dry booster through the lumen.

In Example 4 below, a 1 mm×2000 mm TEFLON™ lumen was used rather than the 1 mm×500 mm stainless steel lumen of Example 3. The dependence of sterilization efficiency with evacuation pressure and evacuation time was studied.

EXAMPLE 4

Dependence of Sterility Results on Evacuation Pressure, Evacuation Time, Presence of a Dry Booster, and Volume Ratio of Dry Booster to Lumen With a TEFLON™ Lumen (No. of Positives/No. of Samples)

| Evacuation Conditions | | Sterility Results | | | |
|---|---|---|---|---|---|
| | | No | Volume Ratio of Dry Booster to Lumen | | |
| Evacuation Pressure | Evacuation Time | Booster | 3:1 | 2:1 | 1:1 |
| 0.4 torr | 0 minutes | 3/3 | 0/3 | 1/3 | — |
| 0.1 torr | 20 minutes | 1/2 | 0/2 | 0/2 | 2/2 |

Even with a dry booster volume:lumen volume of 3:1, all of the biological indicators in the 1 mm×2000 mm TEFLON™ lumens were sterilized with evacuation pressures of 0.4 and 0.1 torr. By contrast, when a 1 mm×500 mm stainless steel lumen was sterilized in Example 3, not all of the biological indicators were sterilized even with dry booster having a volume 5 times larger than the lumen. The stainless steel lumen was shorter than the TEFLON™ lumen, and the dry booster in the stainless steel lumen experiments had a higher volume relative to the volume of the lumen. Both the shorter length of the stainless steel lumen and the larger volume of the dry booster in the experiments in Example 2 should have improved the sterilization efficiency. Instead, the sterilization efficiency with the longer TEFLON™ lumen and the smaller dry booster of Example 4 was higher than with the stainless steel lumen in Example 3.

Further, when the chamber was evacuated to 0.1 torr for 20 minutes, sterilization of the TEFLON™ lumen was effective even when the ratio of the volume of the dry booster (adaptor 20 and vial 30) relative to the lumen 10 was as low as 2:1.

It is believed that the improved sterilization efficiency with the TEFLON™ lumen in Example 4 is due to the TEFLON™ lumen being less reactive with the hydrogen peroxide vapor. The comparative results of Examples 3 and 4 demonstrate that TEFLON™ lumens are easier to sterilize than stainless steel lumens.

The results of Examples 1–4 demonstrate that use of the "dry booster" can enhance the sterilization of the interior of lumens. Further, the ratio of the volume of the "dry booster" relative to the volume of the lumen required for sterilization of the interior of the lumen varies depending on the process conditions and the type of lumen to be sterilized. A volume ratio of 12:1 was required with evacuation pressures of 0.4 torr with no hold time with a stainless steel lumen, as shown in Example 2. When the pressure was reduced to 0.1 torr and the evacuation time was increased to 20 minutes, a volume ratio of 3:1 was required, as shown in Example 3. Sterilization of a TEFLON™ lumen at 0.1 torr and 20 minutes evacuation time was effective with a dry booster volume: lumen volume of 2:1, as shown in Example 4. The sterilization efficiency with a "dry booster" therefore depends on both the process conditions and the type of lumen to be sterilized. Plasma may optionally be introduced to enhance the sterilization.

Figure 14:
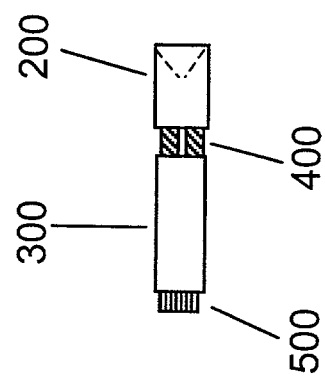
FIG. 14 is a schematic diagram of a lumen attached to an adaptor which is connected to a flow restrictor and a vessel according to a preferred embodiment of the invention, where the vessel has a check valve.

FIG. 14 shows an alternative form of the "dry booster" with some enhancements over the "dry booster" of FIG. 13. The "dry booster" of FIG. 14 comprises an adaptor 200 and a vial 300 as does the "dry booster" of FIG. 13. The "dry booster" shown in FIG. 14 additionally comprises a flow restrictor 400 between the adaptor 200 and the vial 300. The flow restrictor 400 limits the flow of the antimicrobial vapor through the lumen 100, helping to maintain the pressure difference between the vial 300 and the lumen 100.

Further, the "dry booster" shown in FIG. 14 further comprises a check valve 500 on the vial 300. The check valve 500 allows the gas inside the vial 300 to be released from the vial 400 directly into the sterilization chamber rather than having to be evacuated through the lumen 100. The check valve 500 therefore reduces the length of time required to evacuate the vial 300.

The embodiments of the dry booster and the methods of sterilizing devices with the embodiments of the dry booster provide enhanced methods of sterilizing the interior of lumens without the need to attach boosters containing antimicrobial solutions.

The enhanced sterilization efficiency with the dry booster is probably due to the internal volume of the dry booster and the initial pressure difference between the inside and outside of the dry booster. The volume and the pressure act as a driving force to cause the flow of germicide into the booster through the lumen. The dry booster can also be applied to a liquid phase process or a process at a pressure higher than atmospheric pressure by creating a higher pressure outside the booster than inside the booster. The amount of germicide flow into the booster can be controlled by the volume of the booster. The liquid, gas, or vapor process can be enhanced by reducing the pressure in the booster and the lumen before introducing the germicide.

Another aspect of the invention involves a system for sterilizing a lumen, where the system includes a vacuum chamber, a pump to evacuate the chamber, a dry booster, where the dry booster is attachable to and detachable from the lumen, and a source of germicide. Preferably, the dry booster comprises an adaptor that contacts the lumen in a contact area. Preferably, the dry booster encloses an internal volume that is greater than the internal volume of the lumen. More preferably, the internal volume of the dry booster is at least 2 times the volume of the lumen.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. A method for sterilizing a lumen, comprising
providing a dry booster, a connecting device, and a lumen;
connecting a first end of the lumen to the dry booster with the connecting device, wherein the lumen contacts the connecting device at a contact area;
placing the dry booster, the connecting device, and the lumen into a chamber, wherein the chamber is at a pressure;
introducing an antimicrobial vapor or gas into the chamber;
causing the antimicrobial vapor or gas to penetrate the contact area and the lumen; and
sterilizing the lumen.

2. The method of claim 1, wherein the connecting device, at least in the contact area, is permeable to a germicide.

3. The method of claim 1, wherein the surface of the connecting device in the contact area is textured or uneven.

4. The method of claim 1, wherein the dry booster encloses an internal volume that is greater than the internal volume of the lumen.

5. The method of claim 1, further comprising reducing the pressure in the chamber, thereby at least partially evacuating the dry booster.

6. The method of claim 1, further comprising creating a higher pressure outside the dry booster than inside the dry booster; and flowing the antimicrobial vapor or gas from the chamber into the dry booster through the lumen.

7. The method of claim 6, further comprising reducing the pressure in the chamber after the flowing of the antimicrobial vapor or gas from the chamber into the dry booster through the lumen, thereby causing at least a portion of the antimicrobial vapor or gas in the dry booster to flow from the dry booster through the lumen and into the chamber.

* * * * *